(12) United States Patent
Avrahami

(10) Patent No.: US 6,328,033 B1
(45) Date of Patent: Dec. 11, 2001

(54) POWDER INHALER

(76) Inventor: Zohar Avrahami, 40 Binyamin Street, Rehovot 76241 (IL)

( * ) Notice: Subject to any disclaimer, the term of this patent is extended or adjusted under 35 U.S.C. 154(b) by 0 days.

(21) Appl. No.: 09/326,111

(22) Filed: Jun. 4, 1999

(51) Int. Cl.⁷ .................................................. A61M 16/00
(52) U.S. Cl. ............................ 128/203.15; 128/203.12; 128/203.23; 128/203.19; 128/200.25; 128/202.26; 604/58
(58) Field of Search ................. 128/203.12, 203.15, 128/203.19, 203.23, 200.23, 202.25, 202.26; 604/58

(56) References Cited

U.S. PATENT DOCUMENTS

| | | | |
|---|---|---|---|
| 3,844,451 | * 10/1974 | Parker | 222/193 |
| 4,188,907 | * 2/1980 | Lipani | 118/657 |
| 4,648,393 | * 3/1987 | Landis et al. | 128/200.23 |
| 5,193,745 | * 3/1993 | Holm | 239/102.2 |
| 5,221,025 | * 6/1993 | Privas | 222/1 |
| 5,297,542 | * 3/1994 | Bacon | 128/200.14 |
| 5,320,714 | * 6/1994 | Brendel | 128/203.15 |
| 5,405,050 | * 4/1995 | Walsh | 222/1 |
| 5,474,059 | * 12/1995 | Cooper | 128/200.22 |
| 5,483,953 | * 1/1996 | Cooper | 128/200.22 |
| 5,487,378 | * 1/1996 | Robertson et al. | 128/200.16 |
| 5,505,195 | * 4/1996 | Wolf et al. | 128/203.15 |
| 5,694,920 | * 12/1997 | Abrams et al. | 128/200.16 |
| 5,938,118 | * 8/1999 | Cooper | 239/102.2 |
| 6,055,979 | * 5/2000 | Fuchs | 128/203.15 |

FOREIGN PATENT DOCUMENTS

WO 97/47346  12/1997  (WO) .
WO 97/47347  12/1997  (WO) .

* cited by examiner

Primary Examiner—John G. Weiss
Assistant Examiner—Mital Patel
(74) Attorney, Agent, or Firm—Rosenman & Colin LLP (57) ABSTRACT

An inhaler device for administration of a dry powder to a patient includes a package containing a dose of the dry powder and a magnetic field generator, which produces a magnetic field in a vicinity of the package. The magnetic field causes motion of particles of the powder so as to deaggregate the powder in the package, whereby the powder is inhaled by the patient. Preferably, the package includes walls made of a flexible material, which vibrate under the influence of the magnetic field so as to impart the motion to the particles.

36 Claims, 6 Drawing Sheets

POWDER INHALER

FIELD OF THE INVENTION

The present invention relates generally to drug delivery devices, and specifically to devices and methods for delivery of drugs by inhalation.

BACKGROUND OF THE INVENTION

Drug delivery by inhalation is well known in the treatment of respiratory disorders, such as asthma. Inhalation has also found use in delivery of systemic drugs through the lungs, wherein the drugs are absorbed directly into the blood stream without having to pass through (and be broken down by) the digestive tract.

Ultra-fine, dry powders, also known as micro- and nano-powders, are the subject of increasing interest in pharmaceutical manufacturing, because they provide a solution to many of the shortcomings of blended drugs. Active drug ingredients are produced, packaged and administered to the patient as pure, dry powders, without blending them with solvents or other agents. Elimination of the blending steps simplifies the manufacturing process, reduces development and manufacturing costs, makes dosage more accurate, and extends the drug's shelf life.

Dry powder inhalers are known in the art, for delivery of dry powder medications to the lungs. For optimal penetration and absorption in the lungs, the powder particles should be particularly fine—on the order of 4 µm in size, or less. The drawback of such ultra-fine, dry powders is that they are difficult to handle, tending to clump and stick in storage and to scatter when disturbed by even slight air movements. These handling problems must be overcome if dry powder drugs are to be used efficiently and safely, and special methods must be used for accurate dose processing and administration.

PCT patent publications WO 97/47346 and WO 97/47347, which are incorporated herein by reference, describe inhaler apparatus for use with fine powders. A dry powder inside the inhaler apparatus initially adheres to a substrate surface therein. When a patient using the apparatus inhales, an electrostatic field is triggered inside the inhaler. The field causes the powder to be lifted from the surface and drawn into the patient's mouth. To be handled in this manner, the powder must be pre-charged. For practical field intensities (in a hand-held device that is inserted in the patient's mouth), the amount of powder that can be delivered is limited. Furthermore, application of the field must be precisely timed relative to the patient's inhalation to avoid scattering the powder, and the air flow trigger required for this purpose is costly and complex.

MicroDose Technologies Inc., of New Jersey, offers a dry powder inhaler based on the general principles described in the above-mentioned PCT publications. In addition to the used of a timed electrostatic field, the MicroDose inhaler uses a piezoelectric vibrator, brought into contact with a blister pack containing the powder, to deaggregate the particles. The mechanical interface for transferring the vibrations to the powder in the pack is inefficient and further increases the cost and complexity of the inhaler.

SUMMARY OF THE INVENTION

It is an object of the present invention to provide improved devices and methods for delivery of dry powders to a patient by inhalation.

It is a further object of some aspects of the present invention to provide a dry powder inhaler device that deaggregates the powder without the need for a direct mechanical interface to transfer vibrations to a package containing the powder.

It is yet a further object of some aspects of the present invention to provide a dry powder inhaler device from which the powder is released during inhalation by a patient using of the device, without the need for an air flow sensor or other means of active synchronization with the patient's respiration.

It is still a further object of some aspects of the present invention to provide a multi-dose dry powder inhaler device, and Particularly such a device that allows convenient tracking of dosage and patient compliance.

In preferred embodiments of the present invention, a dry powder For delivery to a patient by inhalation is contained in a package having an opening through which the powder flows when the patient inhales. The powder is deaggregated and mobilized by application of a magnetic field. Preferably, the field interacts with the package, engendering rapid motion thereof, which deaggregates the powder.

According to an other aspect of the present invention, an electrostatic valve screen is created by means of an alternating electrostatic field in a vicinity of the opening, so as to trap particles of the powder and prevent their escape from the package except during inhalation.

In some preferred embodiments of the present invention, the alternating electrostatic field is applied using electrodes at either side of the opening. Only when air is made to flow through the opening at a rate above a given threshold, which is generally determined by the voltage applied between the electrodes, can the powder flow out through the electrostatic valve screen. The voltage is preferably set so that the flow rate passes the threshold when the patient inhales, whereby the powder is drawn out of the package and into the patient's lungs.

In some preferred embodiments of the present invention, the package comprises flexible side walls, which are made to vibrate by application of the magnetic field. The vibration of the walls deaggregates the powder in the package and generates air flow which suspends the powder in the air inside the package.

In some of these preferred embodiments, the side walls of the package are coupled to electrical wiring, preferably to coils in the form of electrical conductors applied to a surface of the walls in the manner of a flexible printed circuit. One or more permanent magnets apply a fixed magnetic field to the package. The coils on the walls of the package are driven by an alternating electrical current, generating a field that interacts with the fixed magnetic field and thus causes the walls to vibrate. Preferably, the walls comprise an array of coils, which are driven cooperatively to control the mode of vibration of the walls and thus regulate the air flow inside the package.

Preferably, the external magnetic field has a component in a direction perpendicular to a coil axis, in the plane of the coils, causing the walls to vibrate along the axis. Alternatively or additionally, the magnetic field has a component perpendicular to the plane of the coils, causing lateral vibrations.

In other preferred embodiments, the side walls of the package comprise a magnetic material, which is preferably coated on a surface of the walls. The magnetic field is applied by driving an electromagnet outside the package with an alternating current, which thus causes the walls to vibrate.

Preferably, the flexible side walls are made to vibrate at a resonant vibration frequency thereof, in order to maximize the vibrational energy. Most preferably, a frequency of the alternating current applied to the coils on the walls or to the electromagnet is set so as to engender the resonant vibration. In a preferred embodiment, the frequency of the alternating current is swept through a range of frequencies, preferably including the resonant frequency, and is then set at the Frequency that maximizes the effectiveness of deaggregation, which is typically the frequency that maximizes the wall vibration. For this purpose, a vibration sensor is preferably coupled to the wall and provides feedback for use in controlling the frequency of the alternating current. In another preferred embodiment, the vibration sensor is coupled in a positive feedback loon to a driver that provides the alternating current, causing the loop to spontaneously oscillate at or near the resonant frequency.

In still other preferred embodiments of the present invention, the powder particles comprise an electrically-or magnetically-active component, preferably in the form of a coating on or a compound in the particles. In some of these preferred embodiments, in which the particles are magnetically active, the application of the magnetic field deaggregates the particles without the necessity of vibrating the walls of the package. Preferably, the field is driven to alternate at or near a resonant motion frequency of the particles.

In other preferred embodiments, the electrically-active component enables charging of the particles with a low work function, by contact of the particles with a conductive area or the walls. The charged particles then interact with the electrostatic screen with enhanced efficiency.

In some preferred embodiments of the present invention, a powder inhaler device, operating as described hereinabove, comprises a disposable package, which is introduced into and actuated by a reusable control and power unit. Preferably, the package is a part of a multi-dose cartridge, which most preferably comprises multiple packets of the dry powder, which are actuated in succession. In a preferred embodiment, the control and power unit includes a dose counter, as well as an appropriate user interface, which informs and reminds a patient as to dosage to be administered. The dose counter can also be used to record patient dosage and compliance data to be read out subsequently by medical caregivers.

There is therefore provided, in accordance with a preferred embodiment of the present invention, an inhaler device for administration of a dry powder to a patient, including:

a package containing a dose of the dry powder; and a magnetic field generator, which produces a magnetic field in a vicinity of the package, causing motion of particles of the powder so as to deaggregate the powder in the package, whereby the powder is inhaled by the patient.

Preferably, the package includes walls made of a flexible material, which vibrate under the influence of the magnetic field so as to impart the motion to the particles.

Further Preferably, the package includes electrical wiring coupled to at least one of the walls and a control unit which drives a time-varying current through the wiring, causing the walls to vibrate due to interaction of the current with the magnetic field. Most preferably, the wiring includes a circuit trace printed on at least one of the walls, which forms a plurality of coils. In a preferred embodiment, the control unit drives the plurality of coils at respective relative phases so as to induce a desired mode or vibration of the at least one of the walls.

Alternatively, the walls include a magnetic material, and the field generator includes an electromagnet, which produces a time-varying magnetic field, causing the walls to vibrate due to interaction of the magnetic material with the magnetic field. Preferably, the magnetic material includes a coating on the one or more of the walls.

In a preferred embodiment, the walls made of the flexible material include opposing side walls of the package, which vibrate in a controlled mutual phase relationship. Preferably, the opposing side walls are driven to vibrate in phase or alternatively, in mutually opposite phases so as to pump the powder out of the package.

Preferably, the walls are driven to vibrate at a frequency approximately equal to a resonant vibration frequency thereof. In a preferred embodiment, the device includes a driver circuit, which provides an alternating current of adjustable frequency to drive the vibration of the walls, and a vibration transducer coupled to one of the walls, which transducer provides feedback to the driver circuit, so that the frequency of the alternating current is adjusted such that the walls vibrate at approximately the resonant vibration frequency. Preferably, the driver circuit and transducer are arranged in a self-oscillating positive feedback loop.

In another preferred embodiment, the device includes a vibration sensor, which generates signals responsive to vibration of the walls, and a control unit, which receives the signals from the vibration sensor and, responsive thereto, controls the inhaler device so as to regulate an energy of vibration of the walls. Preferably, the control unit provides an alternating current of adjustable frequency to drive the vibration of the walls, and adjusts the frequency of the alternating current in order the maximize the energy of vibration.

In a preferred embodiment, the powder includes magnetized particles, and the field generator produces a time-varying magnetic field which interacts with magnetic fields of the particles, causing the particles to move. Preferably, a frequency of the time-varying magnetic field is adjusted so that the particles oscillate at appximatelly a resonant frequency thereof.

In still another preferred embodiment, the package includes a multi-dose cartridge, such that multiple doses of the dry powder are administered to the patient in succession, and the device includes a dose counter which tracks the administration of the doses.

There is further provided, in accordance with a preferred embodiment of the present invention, an inhaler device for administration of a dry powder to a patient, including:

a package containing a dose of the dry powder and having an opening through which the powder exits the package and is inhaled by the patient; and an electrostatic valve screen, which traps the powder inside the package by generating a time-varying electrostatic field across the opening.

Preferably, the valve screen includes a pair of electrodes positioned on opposing sides of the opening.

Further preferably, the electrostatic valve screen allows the powder to pass through the opening when a rate of air flow through the opening exceeds a predetermined threshold, wherein the threshold is chosen such that inhalation by the patient generates an air flow through the opening in excess of the threshold.

Preferably, the electrostatic field causes particles of the powder to oscillate in a vicinity of the opening.

There is also provided, in accordance with a preferred embodiment of the present invention, a method for deaggregation of a dry powder for administration to a patient, including applying a magnetic field so as to cause motion of particles of the powder, whereby the powder is inhaled by the patient.

Preferably, the powder is contained in a package having walls made of a flexible material, and applying the magnetic field includes magnetically inducing vibration of the walls so as to impart the motion to the particles. Further preferably, inducing the vibration includes driving a time-varying current in wiring coupled to at least one of the walls, which current interacts with the magnetic field to induce the vibration of the walls. In a preferred embodiment, driving the current includes driving current in different portions of the wiring at respective, relative phases so as to induce a desired mode of vibration of the walls.

Alternatively, inducing the vibration includes applying a time-varying magnetic field, which interacts with magnetic material in the walls to induce the vibration.

In a preferred embodiment, inducing the vibration includes controlling relative phases of vibration of different ones of the walls.

In a further preferred embodiment, inducing the vibration includes driving the vibration at approximately a resonant vibration frequency of the walls. Preferably, inducing the vibration includes sensing vibration of one of the walls and adjusting a frequency of the vibration responsive to the sensing.

In still another preferred embodiment, the method includes magnetizing the particles, wherein applying the magnetic field includes applying a time-varying magnetic field which interacts with magnetic fields of the particles, causing the particles to move.

There is additionally provided, in accordance with a preferred embodiment of the present invention, a method for administration of a dry powder to a patient, including:

providing the dry powder in a package having an opening through which the powder exits the package and is inhaled by the patient; and generating a time-varying electrostatic field across the opening so as to trap the powder inside the package until the patient inhales.

Preferably, generating the field includes adjusting the strength of the field so as to allow the powder to pass through the opening only when a rate of air flow through the opening exceeds a predetermined threshold, wherein the threshold is chosen such that inhalation by the patient generates an air flow through the opening in excess of the threshold.

Further preferably, generating the electrostatic field causes particles of the powder to oscillate in a vicinity of the opening.

The present invention will be more fully understood from the following detailed description of the preferred embodiments thereof, taken together with the drawings in which:

DETAILED DESCRIPTION OF PREFERRED EMBODIMENTS

Figure 1:
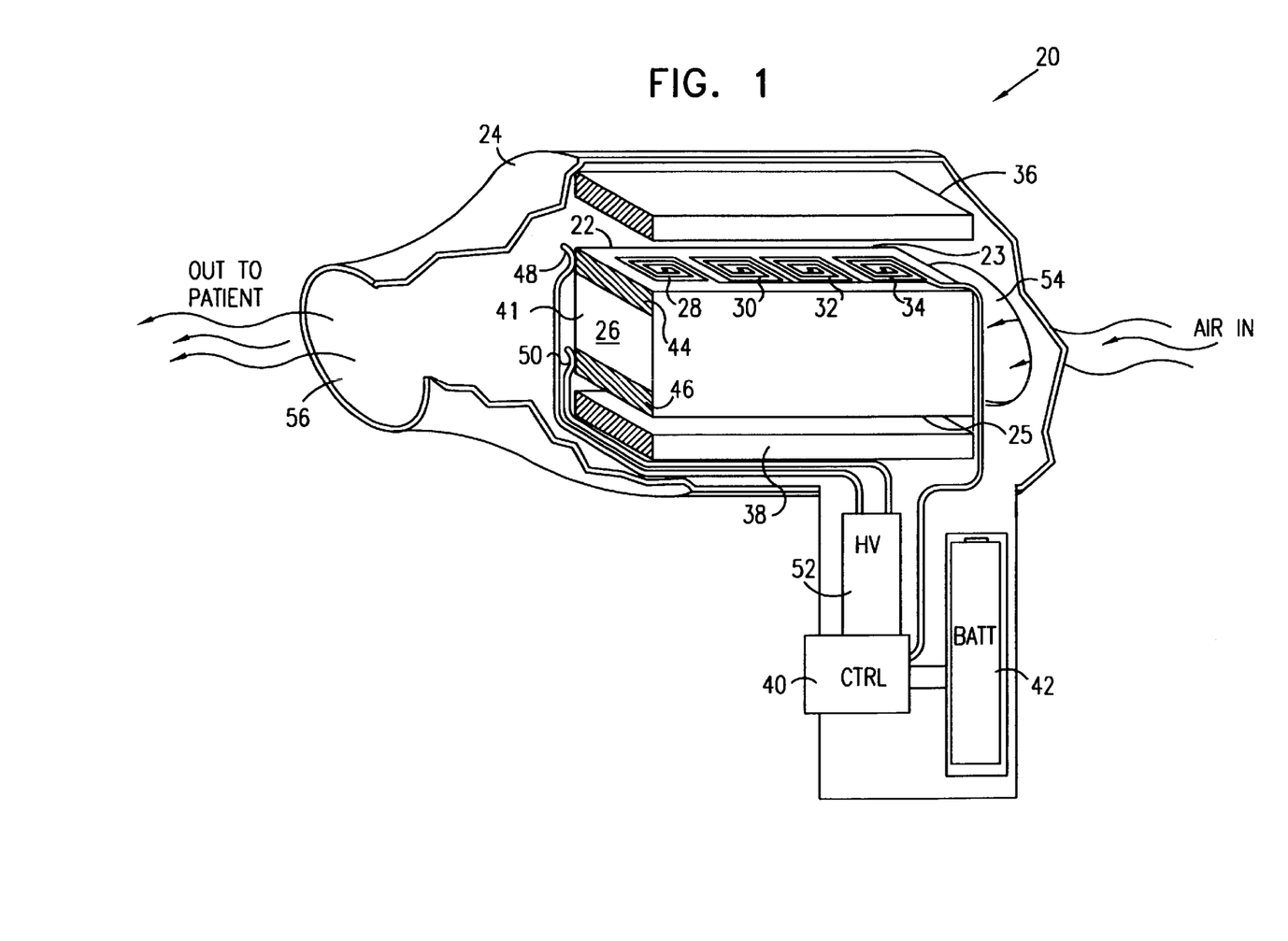
FIG. 1 is a schematic, partly cutaway, pictorial illustration of an inhaler device, in accordance with a preferred embodiment of the present invention.
Figure 2:
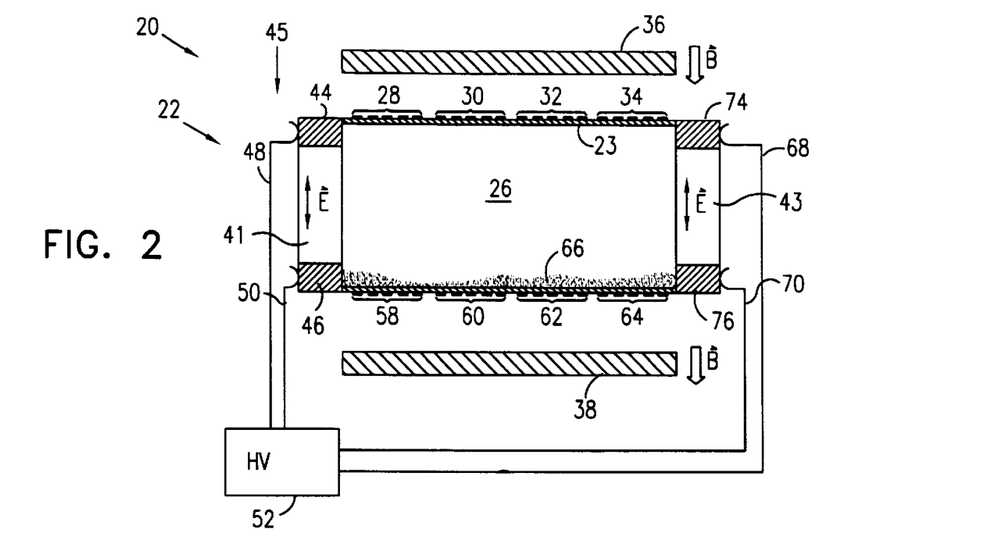
FIG. 2 is a schematic, sectional illustration showing details of a powder package within the inhaler of FIG. 1, in accordance with a preferred embodiment of the present invention.
Figure 3A:
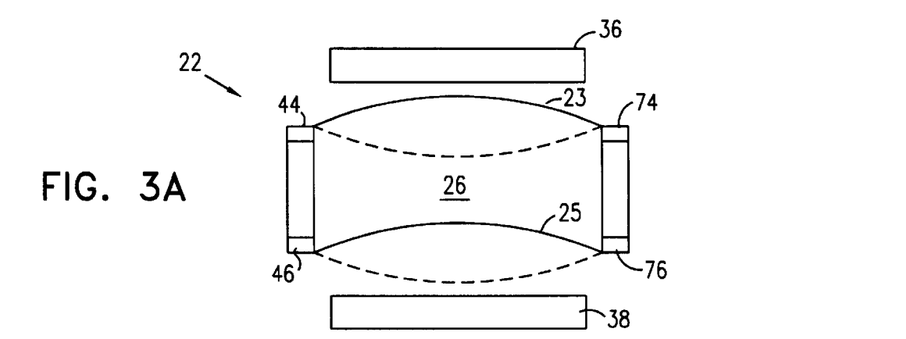
FIGS. 3A, 3B and 4 are schematic illustrations showing operating modes of the package of FIG. 2, in accordance with preferred embodiments of the present invention.
Figure 3B:
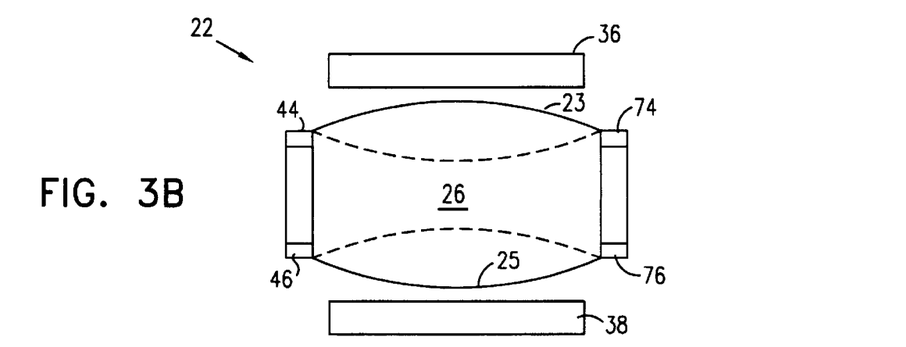
Figure 4:
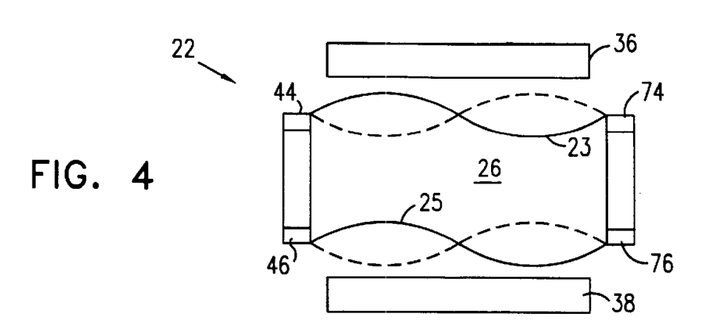

Reference is now made to FIGS. 1 and 2, which schematically illustrate an inhaler device 20, in accordance with a preferred embodiment of the present invention. FIG. 1 is a schematic, partly cutaway, pictorial view, and FIG. 2 is a sectional detail view.

Device 20 comprises a powder package 22, preferably in the form of a disposable, replaceable cartridge, which is inserted into a device housing 24. Package 22 comprises an upper side wall 23 and a lower side wall 25, which enclose a volume 26 in which a medication in the form of a dry powder 66 is contained. The side walls preferably comprise a flexible plastic material, such as Mylar, on which electrical conductors are printed, in the manner of a printed circuit, as is known in the art. The electrical conductors form one or more coils or current loops on each of the side walls. In the embodiment of FIGS. 1 and 2, an upper exterior coil 28, an upper exterior intermediate coil 30, an upper interior intermediate coil 32 and an upper interior coil 34 have the form of traces printed on wall 23, and a lower exterior coil 58, a lower exterior intermediate coil 60, a lower interior intermediate coil 62 and a lower interior coil 64 have the form of traces printed on wall 25. Different numbers of coils or loops, as well as coils and loops of different shapes and forms, may similarly be used.

An upper permanent magnet 36 and a lower permanent magnet 38, or alternatively electromagnets or magnetic materials of other types, are placed adjacent to package 22 and produce a generally static magnetic field in and around the package. More preferably the poles of the magnets are configured to create a magnetic field component perpendicular to the axes of the coils, i.e., in the plane of the walls. In a preferred embodiment, the poles are configured as a North-North pair, with the coils in the gap between the poles. A control unit 40, powered by a battery 42, drives an alternating current through the coils, which interacts with the magnetic fields of magnets 36 and 38 so as to induce vibrations in walls 23 and 25, as described further hereinbelow. Preferably, the frequency of the alternating current is adjusted so that the walls are driven to vibrate at a dominant resonant vibrational frequency of the walls, as ether described hereinbelow. of the alternating current is adjusted so that the walls are driven to vibrate at a dominant resonant vibrational frequency of the walls, as further described hereinbelow.

Optionally, device 20 uses an electrostatic valve screen 45 to prevent escape of particles of powder 66 through openings 41 and 43 except when the patient inhales. The screen takes advantage of the fact that the particles in volume 26 typically acquire an electrostatic charge by contact with the walls of package 22. A high-voltage generator 52 is coupled via an upper contact 48 and a lower contact 50 to drive an upper electrode 44 and a lower electrode 46, respectively, at opposite sides of opening 41, and similarly via contacts 68 and 70 to drive electrodes 74 and 76, respectively, at the sides of opening 43. (Although only a single pair of electrodes is shown at the sides of each opening 41 and 43, it will be understood that multiple electrodes may similarly be used for this purpose.) Preferably, the generator drives the electrodes to produce an alternating electrostatic field in openings 41 and 43 having a peak amplitude of about 3000 volts, at a frequency between 1 and 100 Hz. If the dimensions of package 22 and the characteristics of the field are appropriately chosen, the electrostatic valve screen and the coils on side walls 23 and 25 can be driven at the same frequency, using a common frequency generator in control unit 40.

Optionally, device 20 uses an electrostatic valve screen to prevent escape of particles of powder 66 through openings 41 and 43 except when the patient inhales. The screen takes advantage of the fact that the particles in volume 26 typically acquire an electrostatic charge by contact with the walls of package 22. A high-voltage generator 52 is coupled via contacts 48 and 50 to drive electrodes 44 and 46, respectively, at opposite sides of opening 41, and similarly via contacts 68 and 70 to drive electrodes 74 and 76, respectively, at the sides of opening 43. (Although only a single pair of electrodes is shown at the sides of each opening 41 and 43, it will be understood that multiple electrodes may similarly be used for this purpose.) Preferably, the generator drives the electrodes to produce an alternating electrostatic field in openings 41 and 43 having a peak amplitude of about 3000 volts, at a frequency between 1 and 100 Hz. If the dimensions of package 22 and the characteristics of the field are appropriately chosen, the electrostatic valve screen and the coils on side walls 23 and 25 can be driven at the same frequency, using a common frequency generator in control unit 40.

When the electrostatic field is on, charged particles in the vicinity of openings 41 and 43 oscillate and are trapped in the electrostatic field, as long as the air flow velocity through the openings is below a given threshold. The threshold level is a function of the field strength and frequency and may be adjusted by varying one or both of these parameters. Typically, the threshold air flow velocity is set to about 1 liter/min, and the actual flow rate exceeds this velocity only when the patient inhales. Thus, device 20 releases the powder from package 22 in synchronization with the patient's breath cycle, without the need for a flow sensor or active synchronization.

Figure 5:
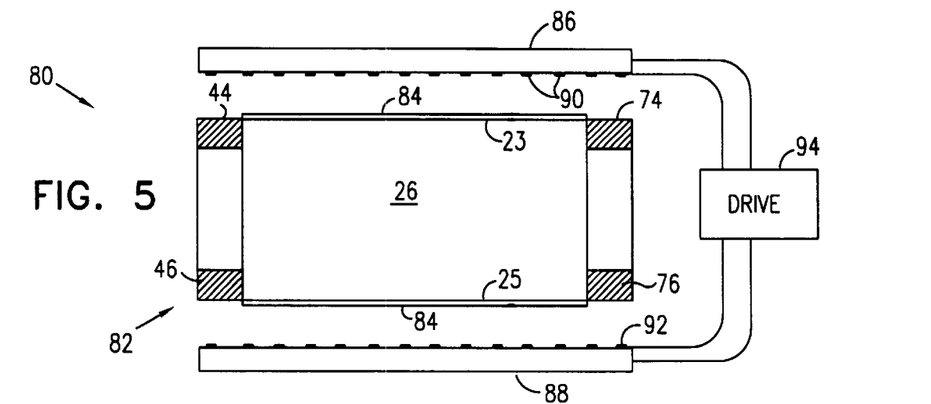
FIG. 5 is a schematic illustration showing details of an inhaler device, in accordance with another preferred embodiment of the present invention.
Figure 6A:
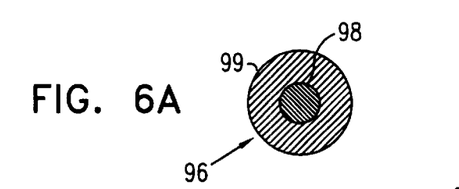
FIG. 6A is a schematic, sectional illustration of a particle of a dry powder for delivery to a patient by inhalation, in accordance with a preferred embodiment of the present invention.
Figure 6B:
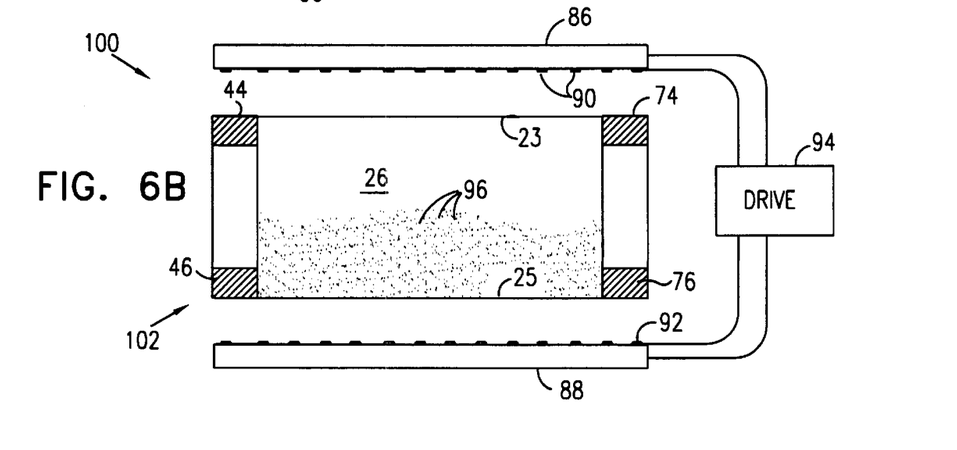
FIG. 6B is a schematic illustration showing details of an inhaler device for delivery of the powder of FIG. 6A, in accordance with a preferred embodiment of the present invention.

Alternatively, mechanical valves, as are known in the art, may be used to close off openings 41 and 43 during times other than the inhalation portion of the patient's breath cycle.

FIGS. 3A and 3B are schematic illustrations showing vibration of side walls 23 and 25 when control unit 40 drives the coils thereon, in accordance with preferred embodiments or the present invention. The solid lines show the side walls at one extremum of their vibration, and the dashed lines show the opposite extremum. The amplitude of the vibration (i.e., the distance between the extrema) is exaggerated for clarity of illustration.

In the embodiment of FIG. 3A, all of coils 28, 30, 32 and 34, together with coils 58, 60, 62 and 64, are driven in phase with one another. Therefore, walls 23 and 25 vibrate in phase with one another, thereby deaggregating and suspending powder 66. Since the vibrations are in phase, the total volume containing the powder is largely constant despite the vibrations, so that there are only minimal pressure variations inside package 22, and the powder is unlikely to be pumped out through one of the openings.

In the embodiment of FIG. 3B, however, the coils on wall 23 are driven in opposite phase to the coils on wall 25. The vibrations of walls 23 and 25 are similarly oppositely phased, thus creating a pumping action that can be used to aid in expelling powder 66 when desired.

FIG. 4A is a schematic illustration showing another mode of vibration of side walls 23 and 25, in accordance with a preferred embodiment of the present invention. In this case, coils 28, 30, 58 and 60 are driven in opposite phase to coils 32, 34, 62 and 64, thus inducing a higher-order vibrational mode of the walls. Other vibrational modes can similarly be induced by appropriately varying the phases and, optionally, amplitudes of the currents used to drive the various coils.

FIG. 5 is a schematic illustration showing details of an inhalation device 80, in accordance with another preferred embodiment of the present invention. Device 80 is largely similar to device 20, described hereinabove, except that it uses a different technique to induce vibration of walls 23 and 25. A package 82 is similar in construction to package 22, except that this package has a magnetic coating 84 on the walls. The coating preferably comprises iron (Fe) or a ferrous compound, for example iron cobalt or gamma Fe2O3, which are widely used in the magnetic recording field. An upper electromagnet 86 and a lower electromagnet 88, respectively comprising an upper coil 90 and a lower coil 92, are placed at either side of package 82. A driver 94 provides an alternating current to the coils, which thus generate a time-varying magnetic field. The field interacts with coating 84 on the side walls, inducing vibration of the walls. There may be multiple adjacent coils on each of electromagnets 86 and 88, like the multiple coils on walls 23 and 25 of package 22. Driver 94 may further control the phase of the currents supplied to the coils so as to vary the spatial distribution of the magnet field and thus affect the vibrational mode of the walls, as described hereinabove.

FIG. 6A is a schematic, sectional illustration of a particle of powder 96, in accordance with still another preferred embodiment of the present invention. The particle preferably comprises a magnetic or electrically-active coating 99 applied around a core 98 containing a medication to be administered to a patient. Alternatively, the particle may comprise a magnetic core, to which the medication is applied as a coating. If the coating is of the electrically-active type, it preferably comprises a substance such as sodium, potassium or calcium, which acquires electrical charge with a low work function by contact with a conductive area of the walls of package 22 or with a suitable electrode in the package. The powder can then be more effectively trapped by the electrostatic valve screen, typically at a lower voltage than would otherwise be required.

FIG. 6B 1s a schematic illustration showing details of an inhalation device 100 for use with particles of powder 96 having a magnetic coating 99, in accordance with a preferred embodiment of the present invention. Device 100 and a powder package 102 therein are substantially similar in design and operation to device 80 and package 82 shown in FIG. 5, except that package 102 does not require magnetic coating 84 on its side walls. Instead, coating 99 of the particles of powder 96 interacts with the time-varying magnetic field generated by coils 90 and 92, causing deaggregation and suspension of the particles in volume 26. There is no need for vibration of side walls 23 and 25 for this purpose, as there is in the other embodiments described hereinabove.

Figure 7:
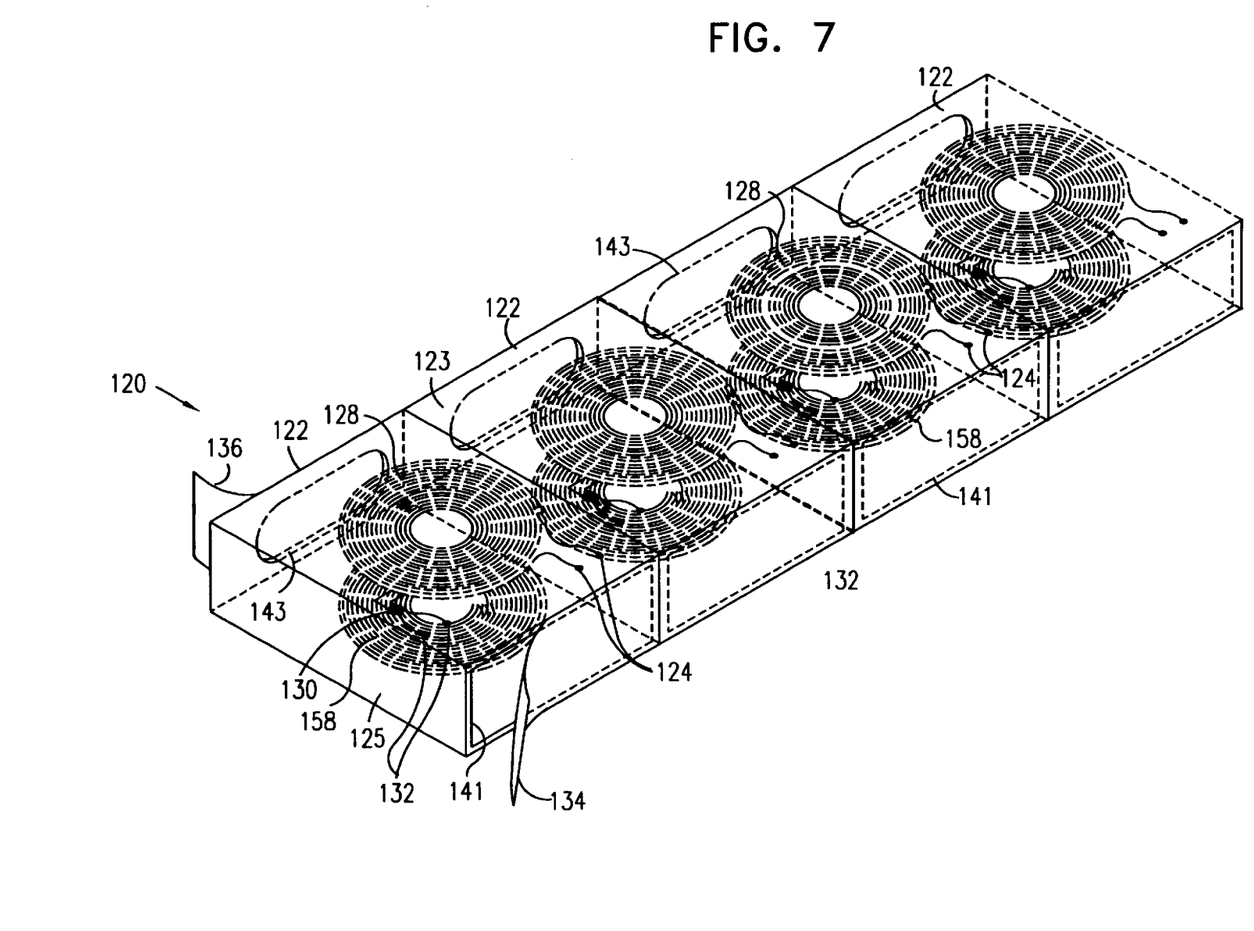
FIG. 7 is a schematic, pictorial illustration of a multi-dose powder dispenser cartridge, in accordance with a preferred embodiment of the present invention.
Figure 8:
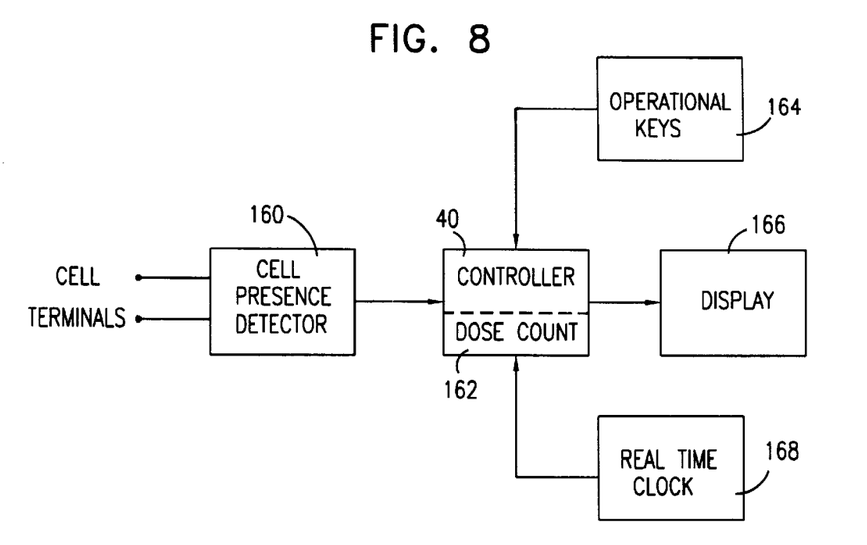
FIG. 8 is a block diagram that schematically illustrates dose counting circuitry used in an inhaler device, in accordance with a preferred embodiment of the present invention.
Figure 9:
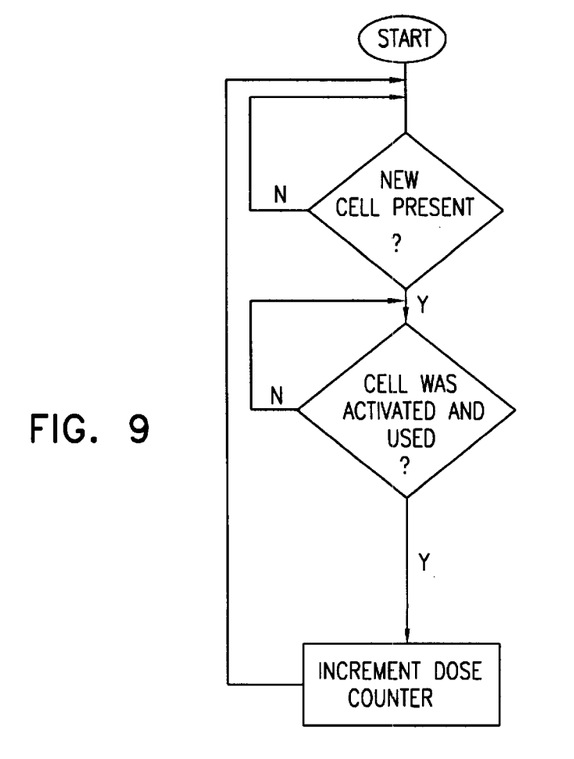
FIG. 9 is a flow chart that schematically illustrates a method for tracking dosage of a medication administered by inhalation, in accordance with a Preferred embodiment of the present invention.
Figure 10:
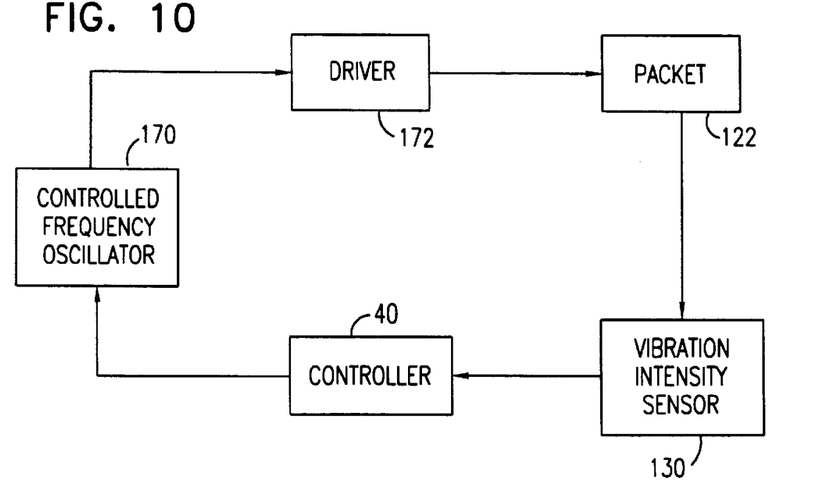
FIG. 10 is a block diagram that schematically illustrates Frequency control circuitry used in driving an inhaler device, in accordance with a preferred embodiment of the present invention.

FIG. 7 is a schematic, pictorial illustration showing a multi-dose powder dispenser cartridge 120, in accordance with a preferred embodiment of the present invention. Cartridge 120 comprises a row of conjoined packets 122 containing a medication in dry powder form, to be dispensed by inhalation using a suitable device having the general form and function of device 20, shown in FIG. 1. Each of packets 122 takes the place of package 22 in device 20, and functions in a generally similar manner. The packets are inserted in succession, as needed, into the inhaler device, preferably without separating the packets in the row one from another. Preferably, cartridge 120 is disposable, and is thrown away after the doses in all of packets 122 have been exhausted, whereas the inhalation device with control and power electronics is reused indefinitely.

When a dose of the medication is to be administered, one of packets 122 is slid into an operating position inside the inhaler device. A first protective strip 134 and a second protective strip 136 are peeled away, uncovering a first air opening 141 and a second air opening 143. An alternating electrical current is driven through coils 128 and 158 on upper and lower walls 123 and 125, respectively, of the packet, via coil contacts 124. (For simplicity of illustration, the contacts for coils 158 are not shown in the figure.) As described hereinabove, the alternating current causes walls 123 and 125 to vibrate, thereby deaggregating the powder.

Preferably, a transducer 130 serves as a vibration sensor, generating signals responsive to the vibration of wall 123, which signals are received via sensor contacts 132 by a controller of the inhalation device, such as control unit 40 of device 20. The transducer signals are used in controlling the alternating current applied to the coils, most preferably to adjust the frequency of the current so as to maximize the energy of wall vibration, as described further hereinbelow. Preferably, transducer 130 comprises a pickup coil, in which a current flows responsive to movement of the coil in the external magnetic field applied to packet 122, for example, by magnets 36 and 38. Alternatively, transducer 130 may comprise an accelerometer or a microphone, which senses acoustic radiation produced by vibration of the walls of the packet (in which case the transducer may also be positioned adjacent to, rather than on, wall 123).

Figure 11:
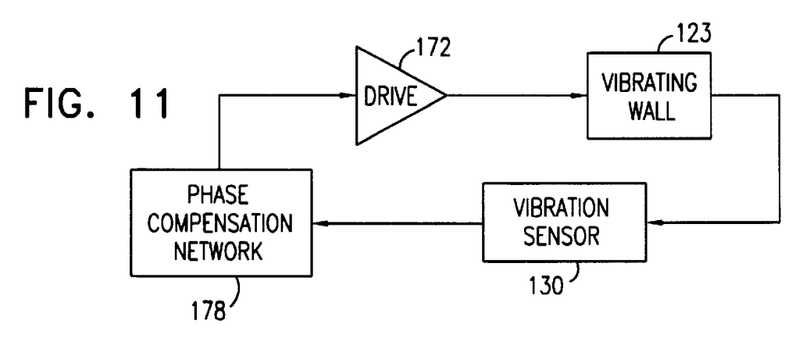
FIG. 11 is a block diagram that schematically illustrates frequency control circuitry used in driving an inhaler device, in accordance with another preferred embodiment of the present invention.

Cartridge 120 is advantageous in that it allows multiple doses to be dispensed in succession, conveniently and reliably. Other cartridge shapes and configurations may similarly be used for this purpose. For example, packets 122 may be arranged in a ring.

FIGS. 8 and 9 schematically illustrate circuitry and methods used in automatically tracking dosage administered by an inhaler device, in accordance with a preferred embodiment of the present invention. FIG. 8 is a block diagram of circuitry used for this purpose, and FIG. 9 is a flow chart illustrating the tracking method. The circuitry and method are preferably, although not necessarily, used in conjunction with a multi-dose cartridge, such as cartridge 120 shown in FIG. 7.

Before the powder dose in one of packets 122 is released, a cell presence detector 160 detects that the packet is properly positioned in a dispensing position in the inhaler device. Detector 160 preferably detects an electrical resistance between contacts 124 or 132 on the packet and, assuming the resistance to be within a predetermined range, notifies control unit 40 of the presence or :he packet. Alternatively, detector 160 may detect a short circuit between suitable, dedicated terminals on the packet (not shown in the figures). Further alternatively, detector 160 may sense the position of packet 122 mechanically or optically, using sensing ,methods known in the art.

Once control unit 40 determines that the packet is suitably positioned, it enables the inhaler device to operate. The device is then actuated by means of operational keys 14 and/or by a flow sensor (not shown), so as to apply electrical current to coils 128 and 158. Preferably, electrostatic valve screens are applied at openings 141 and 143, as described hereinabove, to keep the powder in the packet until it is inhaled by the patient. Bellowing actuation, a dose counter 162, typically comprising a memory segment associated with control unit 40, is incremented to record that the medication was administered. Preferably, the time and date of the dose, as provided by a real-time clock 168, are also recorded in the memory. The patient or medical caregiver can then see on a display 166 a record of doses administered, for purposes of avoiding overdosage or underdosage and or tracking patient compliance. After the dose counter has been incremented, control unit 40 waits for detector 160 co indicate that a new packet 122 has been moved into position before allowing the device to be actuated again.

FIG. 10 is a block diagram that schematically illustrates circuitry used in controlling the frequency of the electrical current applied to coils 128 and 158, in accordance with a preferred embodiment of the present invention. The purpose of controlling the frequency is typically to minimize the vibrational energy of walls 123 and 125 for a given input power to the coils. Such maximal energy is generally achieved when the frequency is such that the walls vibrate at a mechanical resonant frequency thereof. The resonant frequency may vary from packet to packet or from cartridge to cartridge as a result of differences in the dimensions and materials of the packets. For this reason, the circuitry of FIG. 10 is useful in adjusting the frequency for each packet. It will be understood that such circuitry may be applied, as well, to drive the coils of packet 22, shown in FIGS. 1 and 2.

Control unit 40 receives signals from transducer 130, indicative of the amplitude and frequency of vibration of the wall of packet 122. The signals are processed to determine the energy of vibration of the wall, which is generally maximal when the wall is driven to vibrate at its mechanical resonant frequency, as noted above. The control unit varies the frequency of an oscillator 170 (which may also be implemented in software running on the control unit itself), which frequency is supplied to a driver amplifier 172, coupled to coil 128. As the frequency is swept through the resonant frequency of the wall, the control unit detects a corresponding peak in the vibrational energy sensed by sensor 130 and locks onto the peak frequency.

FIG. 11 is a block diagram that schematically illustrates a circuit for use in controlling the frequency of the current applied to coils 128 and 158, in accordance with another preferred embodiment of the present invention. In this case, transducer 130 and driver amplifier 172 are included in a positive feedback loop, coupled by a phase compensation network, as is known in the art. The loop tends to oscillate at a resonant frequency that is determined by the resonant vibration frequency of wall 123, since at this frequency the output signal of transducer 130 is typically maximized. Thus, maximal vibration of the walls of packet 122 (or, similarly, of packet 22) is achieved without the need for active frequency control by control unit 40.

Figure 12:
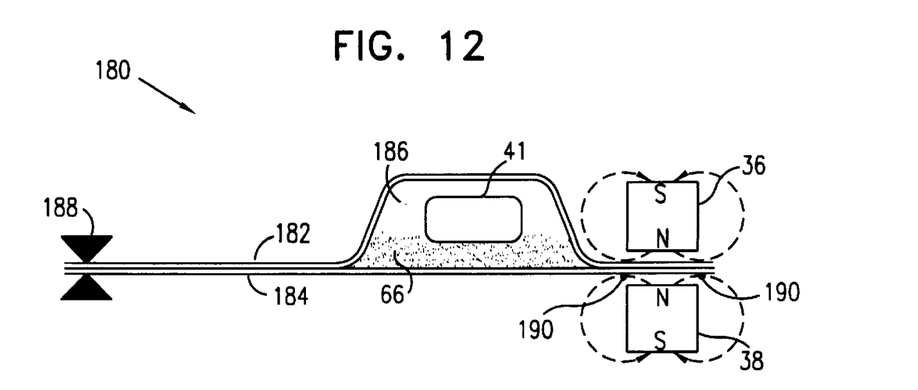
FIG. 12 is a schematic, sectional illustration showing details of a powder package, in accordance with another preferred embodiment of the present invention.

FIG. 12 is a schematic, sectional illustration of a powder package 180, in accordance with another preferred embodiment of the present invention. The package has the form of a blister pack, for ease of manufacture, formed from an upper layer 182 and a lower layer 184 of a suitable plastic material. A blister 186 between the upper and lower layers, having at least one air flow opening 41, holds powder 66. A printed circuit coil 190 is formed on an outer surface of package 180 at one end thereof, which end is positioned between magnets 36 and 38. The other end of the package is held in a holding clip 188. When current flows in coil 190, it causes vibration of the entire package 180, rather than just the walls of blister 186, but the deaggregation effect is substantially similar to that described hereinabove with respect to other preferred embodiments.

It will be appreciated that the preferred embodiments described above are cited by way of example, and the principles of the present invention may similarly be embodied in different configurations and combinations of the elements and concepts shown and described herein. The full scope of the invention is thus limited only by the claims.

What is claimed is:

1. An inhaler device for administration of a dry powder to a patient, comprising:

a package adapted to contain a dose of the dry powder; and a magnetic field generator, operative to produce a magnetic field in a vicinity of the package, causing motion of particles of the powder so as to deaggregate the powder in the package, whereby the powder is inhaled by the patient, wherein the package comprises walls made of a flexible material, which vibrate under the influence of the magnetic field so as to impart the motion to the particles, the device further comprising electrical wiring coupled to at least one of the walls and a control unit coupled to drive a time-varying current through the wiring, causing the walls to vibrate due to interaction of the current with the magnetic field.

2. A device according to claim 1, wherein the wiring comprises a circuit trace printed on at least one of the walls.

3. A device according to claim 1, wherein the wiring comprises a plurality of coils.

4. A device according to claim 3, wherein the control unit drives the plurality of coils at respective relative phases so as to induce a desired mode of vibration of the at least one of the walls.

5. An inhaler device for administration of a dry powder to a patient, comprising:

a package adapted to contain a dose of the dry powder; and a magnetic field generator, operative to produce a magnetic field in a vicinity of the package, causing motion of particles of the powder so as to deaggregate the powder in the package, whereby the powder is inhaled by the patient, wherein the package comprises walls made of a flexible material, which vibrate under the influence of the magnetic field so as to impart the motion to the particles, wherein the walls comprise a magnetic material, and wherein the field generator comprises an electromagnet, which is adapted to produce a time-varying magnetic field, causing the walls to vibrate due to interaction of the magnetic material with the magnetic field.

6. A device according to claim 5, wherein the magnetic material comprises a coating on the one or more of the walls.

7. An inhaler device for administration of a dry powder to a patient, comprising:

a package adapted to contain a dose of the dry powder; and a magnetic field generator, operative to produce a magnetic field in a vicinity of the package, causing motion of particles of the powder so as to deaggregate the powder in the package, whereby the powder is inhaled by the patient, wherein the package comprises walls made of a flexible material, which vibrate under the influence of the magnetic field so as to impart the motion to the particles, wherein the walls made of the flexible material comprise opposing side walls of the package, which vibrate in a controlled mutual phase relationship.

8. A device according to claim 7, wherein the opposing side walls are driven to vibrate in phase.

9. A device according to claim 7, wherein the opposing side walls are driven to vibrate in mutually opposite phases so as to pump the powder out of the package.

10. An inhaler device for administration of a dry powder to a patient, comprising:

a package adapted to contain a dose of the dry powder; and a magnetic field generator, operative to produce a magnetic field in a vicinity of the package, causing motion of particles of the powder so as to deaggregate the powder in the package, whereby the powder is inhaled by the patient, wherein the package comprises walls made of a flexible material, which vibrate under the influence of the magnetic field so as to impart the motion to the particles, wherein the walls are driven to vibrate at a frequency approximately equal to a resonant vibration frequency thereof.

11. A device according to claim 10, and comprising a driver circuit, which provides an alternating current of adjustable frequency to drive the vibration of the walls, and a vibration transducer coupled to one of the walls, which transducer provides feedback to the driver circuit, so that the frequency of the alternating current is adjusted such that the walls vibrate at approximately the resonant vibration frequency.

12. A device according to claim 11, wherein the driver circuit and transducer are arranged in a self-oscillating positive feedback loop.

13. An inhaler device for administration of a dry powder to a patient, comprising:

a package adapted to contain a dose of the dry powder; and a magnetic field generator, operative to produce a magnetic field in a vicinity of the package, causing motion of particles of the powder so as to deaggregate the powder in the package, whereby the powder is inhaled by the patient, wherein the package comprises walls made of a flexible material, which vibrate under the influence of the magnetic field so as to impart the motion to the particles, the device further comprising a vibration sensor, which is adapted to generate signals responsive to vibration of the walls, and a control unit, which is coupled to receive the signals from the vibration sensor and, responsive thereto, to control the inhaler device so as to regulate an energy of vibration of the walls.

14. A device according to claim 13, wherein the control unit provides an alternating current of adjustable frequency to drive the vibration of the walls, and wherein the control unit adjusts the frequency of the alternating current in order to maximize the energy of vibration.

15. An inhaler device for use by a patient, comprising:

a dose of dry powder comprising magnetized particles;

a package adapted to contain the dose of the dry powder; and a magnetic field generator, operative to produce a magnetic field in a vicinity of the package, causing motion of particles of the powder so as to deaggregate the powder in the package, whereby the powder is inhaled by the patient, wherein the field generator is adapted to produce a time-varying magnetic field which interacts with magnetic fields of the particles, causing the particles to move.

16. A device according to claim 15, wherein a frequency of the time-varying magnetic field is adjusted so that the particles oscillate at approximately a resonant frequency thereof.

17. An inhaler device for administration of a dry powder to a patient, comprising:

a package adapted to contain a dose of the dry powder; and a magnetic field generator, operative to produce a magnetic field in a vicinity of the package, causing motion of particles of the powder so as to deaggregate the powder in the package, whereby the powder is inhaled by the patient, wherein the powder comprises magnetized particles, and wherein the field generator is operative to produce a time-varying magnetic field which interacts with magnetic fields of the particles, causing the particles to move.

18. An inhaler device for administration of a dry powder to a patient, comprising:

a package adapted to contain a dose of the dry powder and having an opening through which the powder can exit the package to be inhaled by the patient; and an electrostatic valve screen, arranged to trap the powder inside the package by generating a time-varying electrostatic field across.

19. A device according to claim 18, wherein the valve screen comprises a pair of electrodes positioned on opposing sides of the opening.

20. A device according to claim 18, wherein the electrostatic valve screen allows the powder to pass through the opening when a rate of air flow through the opening exceeds a predetermined threshold.

21. A device according to claim 20, wherein the threshold is chosen such that inhalation by the patient generates an air flow through the opening in excess of the threshold.

22. A device according to claim 18, wherein the electrostatic field causes particles of the powder to oscillate in a vicinity of the opening.

23. A method for deaggregation of a dry powder for administration to a patient, comprising applying a magnetic field so as to cause motion of particles of the powder, whereby the powder is inhaled by the patient.

24. A method according to claim 23, wherein the powder is contained in a package having walls made of a flexible material, and wherein applying the magnetic field comprises magnetically inducing vibration of the walls so as to impart the motion to the particles.

25. A method according to claim 24, wherein inducing the vibration comprises driving a time-varying current in wiring coupled to at least one of the walls, which current interacts with the magnetic field to induce the vibration of the walls.

26. A method according to claim 25, wherein driving the current comprises driving current in different portions of the wirings at respective, relative phases so as to induce a desired mode of vibration of the walls.

27. A method according to claim 24, wherein inducing the vibration comprises applying a time-varying magnetic field, which interacts with magnetic material in the walls to induce the vibration.

28. A method according to claim 24, wherein inducing the vibration comprises controlling relative phases of vibration of different ones of the walls.

29. A method according to claim 24, wherein inducing the vibration comprises driving the vibration at approximately a resonant vibration frequency of the walls.

30. A method according to claim 24, wherein inducing the vibration comprises sensing vibration of one of the walls and adjusting a frequency of the vibration responsive to the sensing.

31. A method according to claim 23, and comprising magnetizing the particles, wherein applying the magnetic field comprises applying a time-varying magnetic field which interacts with magnetic fields of the particles, causing the particles to move.

32. A method according to claim 23, and comprising generating a time-varying electrostatic field so as to trap the powder until it is inhaled by the patient.

33. A method for administration of a dry powder to a patient, comprising:

providing the dry powder in a package having an opening through which the powder exits the package and is inhaled by the patient; and generating a time-varying electrostatic field across the opening so as to trap the powder inside the package until the patient inhales.

34. A method according to claim 33, wherein generating the field comprises adjusting the strength of the field so as to allow the powder to pass through the opening only when a rate of air flow through the opening exceeds a predetermined threshold.

35. A method according to claim 34, wherein the threshold is chosen such that inhalation by the patient generates an air flow through the opening in excess of the threshold.

36. A method according to claim 33, wherein generating the electrostatic field causes particles of the powder to oscillate in a vicinity of the opening.

* * * * *